US011602607B2

(12) United States Patent
Lau et al.

(10) Patent No.: US 11,602,607 B2
(45) Date of Patent: Mar. 14, 2023

(54) SWIVEL CONNECTOR

(71) Applicant: Fisher & Paykel Healthcare Limited, Auckland (NZ)

(72) Inventors: Andrew Chi Lup Lau, Auckland (NZ); Lloyd Dylan Kimble, Auckland (NZ); Richard Daniel Panara, Auckland (NZ); Laurence Gulliver, Auckland (NZ); Brent Ian Laing, Auckland (NZ); Sooji Hope Clarkson, Auckland (NZ); Jason Allan Klenner, Auckland (NZ)

(73) Assignee: Fisher & Paykel Healthcare Limited, Auckland (NZ)

(*) Notice: Subject to any disclaimer, the term of this patent is extended or adjusted under 35 U.S.C. 154(b) by 1493 days.

(21) Appl. No.: 14/861,266

(22) Filed: Sep. 22, 2015

(65) Prior Publication Data

US 2016/0082218 A1 Mar. 24, 2016

Related U.S. Application Data

(60) Provisional application No. 62/198,305, filed on Jul. 29, 2015, provisional application No. 62/077,831, (Continued)

(51) Int. Cl.
*A61M 16/08* (2006.01)
*A61M 16/06* (2006.01)
(Continued)

(52) U.S. Cl.
CPC .... *A61M 16/0816* (2013.01); *A61M 16/0672* (2014.02); *A61M 16/0051* (2013.01); (Continued)

(58) Field of Classification Search
CPC ....... F16L 33/22; F16L 37/08; F16L 2201/44; F16L 37/02; F16L 37/0847; F16L 37/091; (Continued)

(56) References Cited

U.S. PATENT DOCUMENTS 2,258,919 A * 10/1941 Wallace ................. 285/258
3,588,149 A 6/1971 Demler, Sr. et al.
(Continued)

FOREIGN PATENT DOCUMENTS

| EP | 2407103 B1 | 11/2013 |
| GB | 2186652 A | 8/1987 |
| WO | WO 2008/058506 | 5/2008 |

OTHER PUBLICATIONS

International Search Report; PCT/NZ2014/000020; dated May 21, 2014; 3 pages.
Written Opinion; PCT/NZ2014/000020; dated May 21, 2014; 4 pages.

*Primary Examiner* — Matthew Troutman
*Assistant Examiner* — William S. Choi
(74) *Attorney, Agent, or Firm* — Knobbe Martens Olson & Bear, LLP

(57) ABSTRACT

A connector is described that may be configured to connect between a first tube and a second tube. The connector has an internal component and an external component. The external component has a first end and a second end. The first end has an external taper and an internal coupling face that may be configured to interact with the first tube and the second end may be configured to interact with the second tube. The internal component may be configured to rotate independently to the external component. The external component has a gripping region to aid the user in disconnection of the connector. An attachment mechanism may attach the second tube to the internal component.

22 Claims, 8 Drawing Sheets

Related U.S. Application Data filed on Nov. 10, 2014, provisional application No. 62/054,768, filed on Sep. 24, 2014.

(51) Int. Cl.
  *A61M 16/10* (2006.01)
  *A61M 16/00* (2006.01)

(52) U.S. Cl.
  CPC ..... *A61M 16/0069* (2014.02); *A61M 16/0683* (2013.01); *A61M 16/109* (2014.02); *A61M 16/1095* (2014.02); *A61M 2205/3368* (2013.01); *A61M 2205/3653* (2013.01)

(58) Field of Classification Search
  CPC ......... F16L 37/10; F16L 37/14; F16L 37/138; F16L 37/50; F16L 37/0841; F16L 55/1157; A61M 16/0816; A61M 16/1095; A61M 16/0672; A61M 16/0069; A61M 16/109; A61M 16/0051; A61M 16/0683; A61M 2205/3368; A61M 2205/3653; A61M 39/1055; A61M 39/10; A61M 2039/1033; A61M 2039/1027; A61M 2039/1038; A61M 2039/1066; A61M 2039/1016; A61M 16/0875
  USPC .... 285/133.21, 305, 330, 314, 95, 272, 275, 285/308, 358, 921, 121.3, 121.6, 123.5; 604/533, 905
  See application file for complete search history.

(56) References Cited

U.S. PATENT DOCUMENTS

| | | | |
|---|---|---|---|
| 3,684,319 A * | 8/1972 | Samartina | 285/247 |
| 3,768,476 A | 10/1973 | Raitto | |
| 4,026,581 A | 5/1977 | Pasbrig | |
| 4,030,494 A | 6/1977 | Tenczar | |
| 4,254,773 A | 3/1981 | Waldbillig | |
| 4,369,781 A | 1/1983 | Gilson et al. | |
| 4,538,836 A | 9/1985 | Krutten | |
| 5,062,420 A | 11/1991 | Levine | |
| 5,116,088 A * | 5/1992 | Bird | A61M 16/08 128/202.27 |
| 5,176,415 A | 1/1993 | Choksi | |
| 5,279,597 A | 1/1994 | Dassa et al. | |
| 5,312,377 A | 5/1994 | Dalton | |
| 5,509,911 A * | 4/1996 | Cottone, Sr. | A61M 39/1055 604/536 |
| 6,273,087 B1 | 8/2001 | Boussignac et al. | |
| 6,484,724 B1 | 11/2002 | Sloan | |
| 6,874,522 B2 | 4/2005 | Anderson et al. | |
| 6,893,056 B2 * | 5/2005 | Guala | A61M 39/1055 285/332 |
| D558,339 S | 12/2007 | Christopher et al. | |
| 7,329,249 B2 * | 2/2008 | Bonaldo | 604/248 |
| 7,458,615 B2 * | 12/2008 | White | A61M 16/0069 285/272 |
| 8,454,579 B2 * | 6/2013 | Fangrow, Jr. | A61M 39/10 604/539 |
| 8,540,698 B2 | 9/2013 | Spohn et al. | |
| 9,889,288 B2 | 2/2018 | Hoffman et al. | |
| 10,006,573 B2 | 6/2018 | Frame et al. | |
| 2002/0117849 A1 * | 8/2002 | Bailey | A61M 39/1055 285/123.15 |
| 2003/0155765 A1 * | 8/2003 | Thomas | F16L 37/0985 285/305 |
| 2006/0096597 A1 | 5/2006 | Amann | |
| 2007/0073233 A1 * | 3/2007 | Thor | 604/151 |
| 2008/0086087 A1 | 4/2008 | Spohn | |
| 2013/0187381 A1 * | 7/2013 | Guala | A61M 39/10 285/387 |
| 2019/0003625 A1 | 1/2019 | Frame et al. | |

* cited by examiner

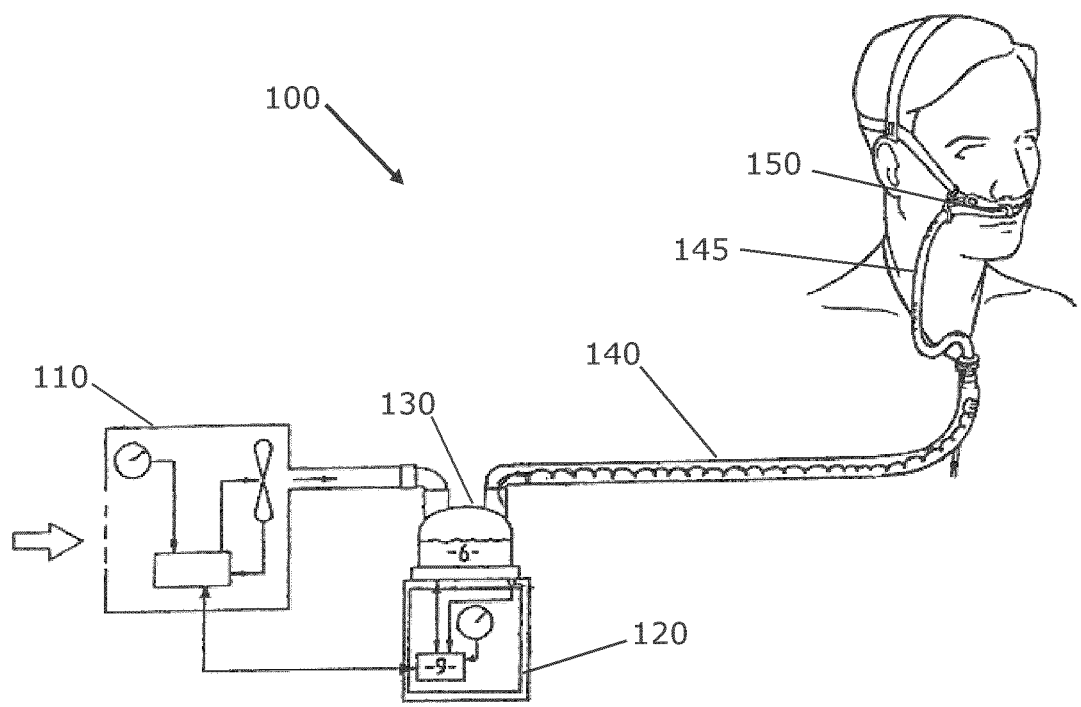
*Figure 1*
*Figure 2*
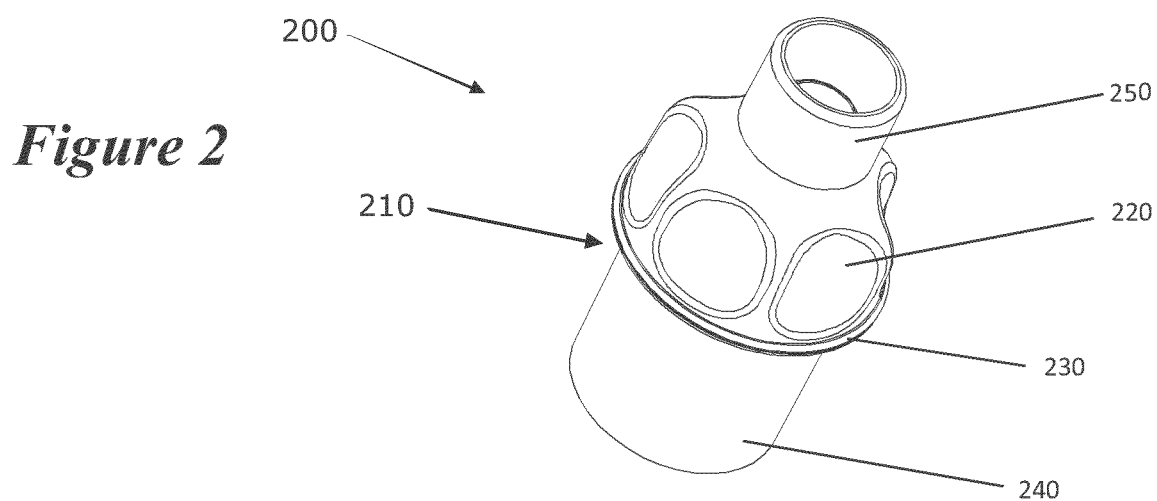

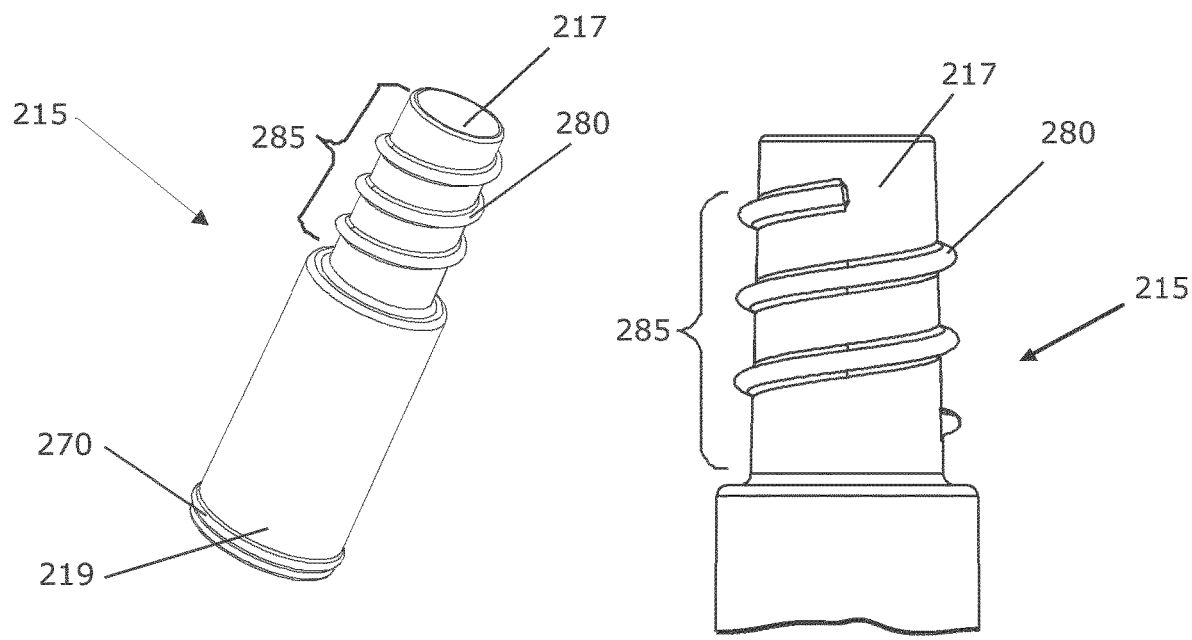
*Figure 5A*  *Figure 5B*
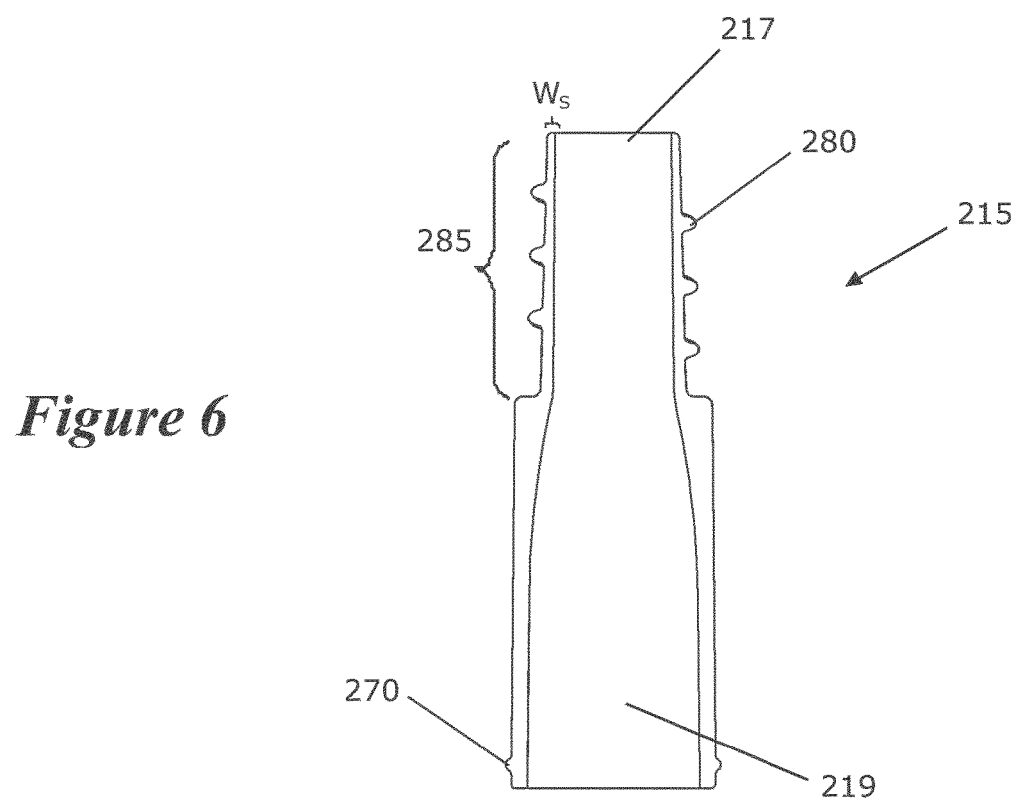
*Figure 6*

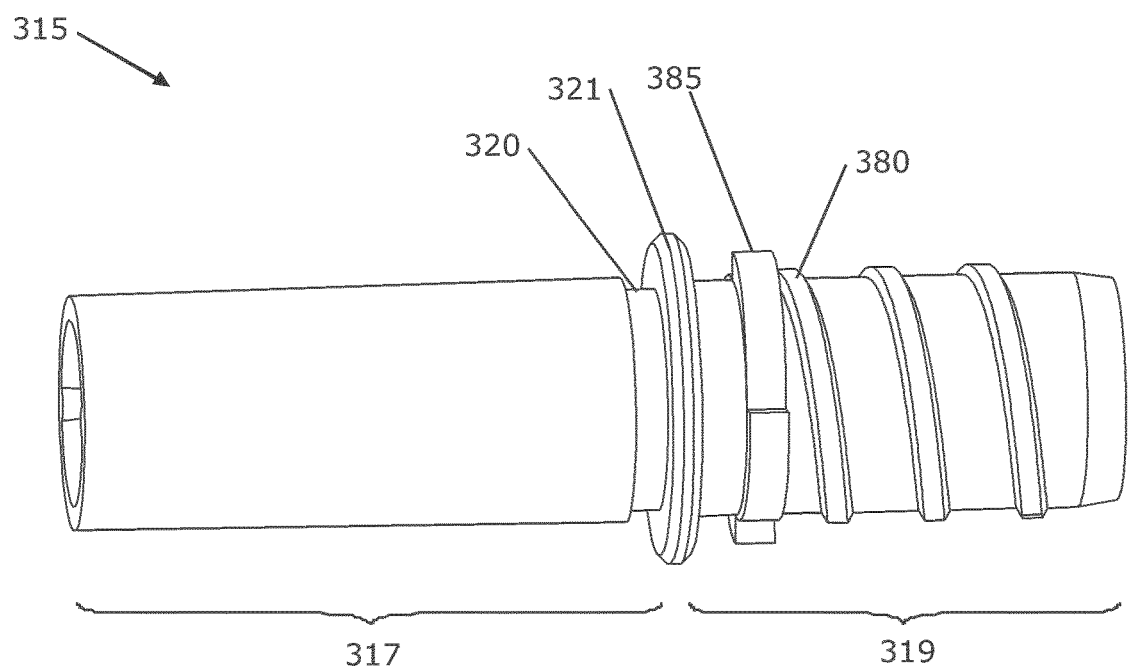
*Figure 9*
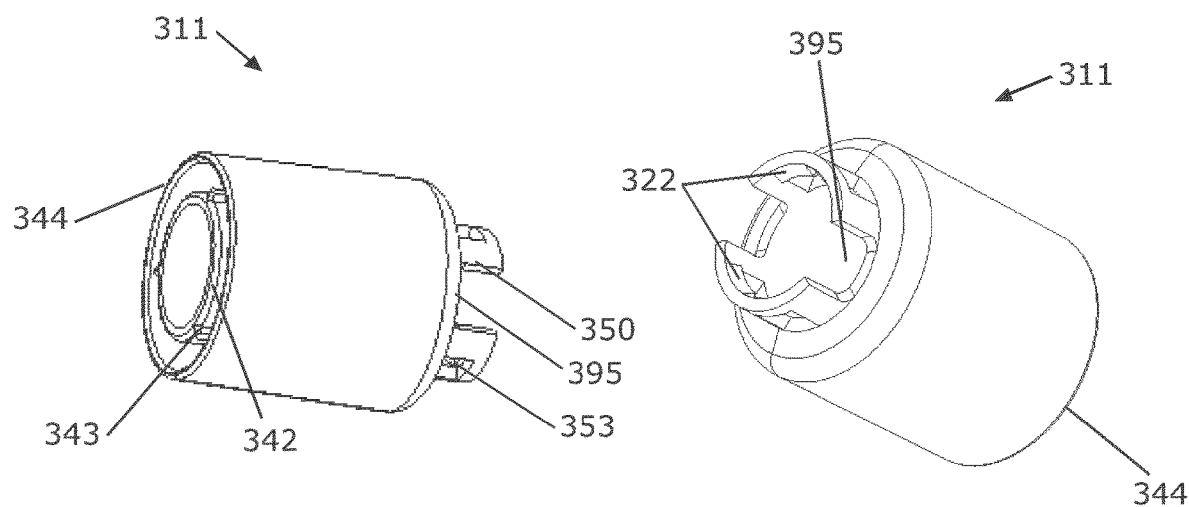
*Figure 10A*          *Figure 10B*

SWIVEL CONNECTOR

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND

Technical Field

The present disclosure generally relates to a connector for a medical system. More particularly, the present disclosure relates to a connector configured for use within a respiratory system.

Description of the Related Art

High flow systems deliver respiratory gases at high flow to a patient via a patient interface, such as a nasal cannula or a mask. Gases may be heated and humidified before being delivered to the patient and, thus, may aim to replicate the transformation of air as it passes through the nose to the lungs of healthy individuals. The gases may be delivered at a broad range of flows and oxygen concentrations to provide a versatile therapy. Flow may be controlled to improve mucociliary clearance and dead space flushing while providing air and/or oxygen to patients. High flow therapy may improve patient comfort when compared with other therapies, for example, invasive ventilation.

Respiratory gases may be delivered via a medical tube to the patient interface. Some systems may comprise multiple medical tubes to form the pathway between the humidification apparatus and the patient interface. A smaller and/or more lightweight medical tube may be used to couple with the patient interface.

BRIEF SUMMARY

Respiratory systems in the prior art may deliver respiratory gases to the patient via multiple medical tubes to form the pathway between the humidification apparatus and the patient interface. One of these medical tubes, for example, an interface tube, may be configured to couple between another medical tube and a patient interface using a coupling mechanism.

Coupling mechanisms enable coupling between an interface tube and a medical tube; however, these may be limited with regards to the coupling interfaces of the medical tubes to which they may be coupled. For example, in some embodiments, an interface tube may only couple with a coupling interface such as a 22 mm female taper breathing circuit connector. Other embodiments comprise a coupling mechanism that may only couple between the interface tube and a proprietary connector, as described in the embodiments disclosed in United States Patent Application No. US2005/077726A1, the contents of which are hereby incorporated by reference in its entirety. Prior coupling mechanisms attach to the interface tube such that they provide a continuous connection between the medical tube and the interface tube. However, in use, a patient may wish to rotate and move their head which may cause the interface tube to become twisted and/or tangled. This can have an effect on the flexibility of the interface tube and the usability of the patient interface because a twisted and/or tangled interface tube causes restricted or limited movement. Further, a twisted or tangled tube can cause a kink in the tube resulting in a flow restriction. This results in discomfort for the patient.

Some prior coupling mechanisms may not sufficiently attach the interface tube to the coupling mechanism such that an application of force during normal use may cause the interface tube to tear or pull off the coupling mechanism.

The forces required to disconnect a coupling mechanism, such as a connector, from a coupling interface may be difficult for a user. A high axial force may be required to remove and/or separate the interface tube from other medical tubes and/or respiratory components. This may contribute to tearing or damage to the interface tube and/or the medical tube.

Some prior coupling mechanisms may be difficult for a user to grip. This is particularly problematic if the user needs to apply a high force to the coupling mechanism to disconnect the coupling mechanism and the coupling interfaces, as the user cannot get a secure grip.

Prior tubing may comprise interface tubes that are breathable to aid in removal of condensate in the interface tube. The breathable interface tubes may, in some cases, absorb the condensate, which may cause a swelling of the interface tube. As a result, coupling mechanisms may not be able to house the swollen interface tube. This may damage the interface tube and/or impair the removal of condensate from the interface tube.

A user may struggle to identify between different sized coupling mechanisms. As a result, when preparing a system, it may be necessary to try several different coupling mechanisms before determining the correct size for the breathing circuit being used. This may be time-consuming and frustrating for the user.

A coupling mechanism is described that at least partially overcomes or ameliorates at least one disadvantage of the prior art, or at least provides a useful choice.

The coupling mechanism comprises a connector. The connector comprises an internal component and an external component that couple together. The external component is configured to interact with different coupling interfaces while the internal component is configured to interact with the interface tube.

The internal component is configured to be coupled with the external component, for example, by a snap-fit connection.

Thus, the external component comprises a coupling face that enables coupling between the coupling mechanism and a plurality of coupling interfaces, for example, a 22 mm female taper and a male connector.

The internal component is rotatably coupled within the external component to maintain freedom of movement for a patient. Thus, if the patient moves or rotates their head during treatment, thereby causing the interface tube to rotate or swivel, the internal component may rotate or swivel in relation to the movement. As a result, the interface tube may not become twisted and/or tangled in use.

In some embodiments a thread on the internal component couples the interface tube with the connector. The portion of the internal component comprising the thread may be tapered to further retain the interface tube. Thus, once the internal component is integrated into the connector, it becomes difficult to remove the interface tube from the internal component. As a result, the interface tube is securely coupled with the connector. In an embodiment the internal component is substantially straight (e.g. does not include a tapered section, or is non-tapered). In an embodiment, an end portion of the internal component is tapered to retain the interface tube.

The connector is configured such that disconnection from a complementary connection portion is easier. For example, the connector is configured such that disconnection from a 22 mm tapered female connection, is easier for the user. The connector is configured to allow a user to apply a torque or a rotational force to disconnect the connector from a complementary connection. For example the connector may be twisted or rotated to break the connection with and then be removed from the 22 mm taper. As a result, the force required to remove the connector is reduced, thereby improving the usability of the system.

Alternatively the connector may be configured for different disconnection mechanisms for different coupling interfaces. For example, the proprietary male connection may be disconnected via a pulling force.

The external component comprises gripping regions to aid a user during connection or disconnection of the connector. The gripping regions comprise one or more indents that receive one or more fingers of a user when the user grips the gripping section. The indents may be substantially concave in shape and include a rounded section. In one form each indent is shaped to substantially conform to the shape of a finger tip.

In some embodiments, the material forming the gripping portions may comprise an opaque or cloudy appearance and/or a rougher finish, which may be a visual indicator to the user to grip these portions.

The internal component is sized such that it can accommodate the interface tube in both a wet and/or dry condition. As a result, moisture and/or condensate within the interface tube may not have a negative effect on the breathability of the interface tube.

The internal component may comprise a visual indicator, for example, different colouring, that can help a user to distinguish between different sizes of the coupling mechanism. In alternative embodiments the visual indicator can be a different pattern, or a different material or any other feature that allows the internal component to be visually distinct from the rest of the connector.

In one embodiment the external component comprises multiple parts, for example, an intermediate component and a cuff. The multiple parts are coupled together to form the external component. Coupling is achieved using snap-fit connections. Alternatively coupling may be achieved by using welding, co-moulding, over moulding or using, adhesives, mechanical interference or welding between the multiple parts.

Alignment features are located on the cuff or the intermediate component. The alignment features improve coupling between the multiple parts, and help to orient the multiple parts in the correct operative alignment to form an effective connector. The alignment features may take the form of ridges, protrusions or indentations.

At least one of the multiple parts comprises gripping regions for the user to grasp during connection or disconnection of the connector. The gripping regions may comprise one or more protrusions or indents to receive the finger tips of the user in use. The gripping regions comprise visual indicators, different textures, or different materials to indicate to the user to grip these portions.

In an embodiment, the internal component comprises a groove to facilitate coupling between the internal component and the external component. At least one of the multiple parts of the external component is configured to couple with the internal component. Coupling may be achieved using a snap-fit connection, wherein a protrusion on the external component may be configured to snap-fit with the groove on the internal component. Alternatively the internal component may comprise a protrusion that can engage with a recess or groove in the external component.

Clearance between the internal component and the external component enables rotation of the internal component relative to the external component. This may aid a user to disconnect the connector.

The internal component comprises thread or adhesive mechanism located on the outer surface of the internal component. A tube can be coupled to the internal component via the thread or adhesive mechanism. In alternative embodiments the thread or adhesive mechanism may be located on the inner surface of the internal component. The coupling between the tube and the internal component may reduce the likelihood of the tube disengaging from the internal component in use.

In some embodiments, the present disclosure relates to a connector for a medical tube or a breathing tube for a respiratory assistance system, comprising:
an internal component and an external component,
wherein the internal component has a first end and a second end, and the external component has a corresponding a first end and a second end,
the first end of the external component comprising an external coupling face and an internal coupling face, and
the second end of the internal component comprising an attachment mechanism configured to attach to a tube, and
wherein the internal component is configured to rotate independently to the external component.

In some embodiments, the external component is a unitary or monolithic or single-piece construction.

In some embodiments, the external component is a two-piece construction, said construction comprising a first piece and a second piece provided in a permanent attachment arrangement with each other once attached to each other.

In some embodiments, the external component comprises a gripping region.

In some embodiments, the external coupling face is configured to connect to a first coupling interface and the internal coupling face is configured to connect to a second coupling interface.

In some embodiments, the connector is configured to couple with at least one of a 22 mm female taper or a proprietary male connector.

In some embodiments, the internal component is coupled to the tube via the attachment mechanism.

In some embodiments, the attachment mechanism comprises a thread on at least part of the internal component.

In some embodiments, the external component comprises a shoulder to provide a region for a user to apply an axial force to the connector and/or an insertion limit to limit a length the external component can be connected with a coupling interface.

In some embodiments, the internal component is coupled to the external component for relative rotation there between via a ridge on the internal component and a corresponding groove on the external component, or a ridge on the external component and a corresponding groove on the internal component.

In some embodiments, the groove or ridge is located adjacent to the first end of the internal component.

In some embodiments, the attachment mechanism is located on an attachment region of the internal component, and the attachment region comprises a tapered profile.

In some embodiments, the tapered profile comprises a proximal end that has a larger diameter than a distal end.

In some embodiments, a property of the connector is determined by visual indicators on the internal component.

In some embodiments, the property of the connector is size.

In some embodiments, the visual indicators comprise at least one of colour, shading or patterns.

In some embodiments, the external component comprises a translucent portion such that the visual indicators are visible to a user.

In some embodiments, the gripping region is at least partially opaque in comparison to the translucent portion of the external component.

In some embodiments, the translucent portion is at a first and/or a second end region of the external component.

In some embodiments, the connector is configured to form part of a high flow system respiratory assistance system.

In some embodiments, the external coupling face comprises an external taper.

In some embodiments, the external coupling face is an outer surface of an outer wall of the external component.

In some embodiments, the internal coupling face is an outer surface of an inner wall of the external component, or an inner surface of the outer wall of the external component.

In some embodiments, the internal and external walls are concentric.

In some embodiments, the external component comprises two internal coupling faces for connecting to a coupling interface.

In some embodiments, the external component comprises a shoulder, the shoulder or shoulders configured to correspond with a protrusion on the coupling interface to enable a snap-fit connection between the coupling interface and the external component. Optionally the shoulder is disposed on the inner surface of the outer wall and/or a shoulder is provided on the outer surface of the inner wall.

In some embodiments, the internal and external components are configured so that a clearance between the internal and external components allows for relative rotation between the internal and external components while providing for a negligible or insignificant level of leakage of gases between the internal and external components at an operating pressure of gases in a lumen of the connector.

In some embodiments, the internal component is coupled to the external component for relative rotation there between via a ridge on the internal component and a corresponding groove on the external component, or a ridge on the external component and a corresponding groove on the internal component, and wherein the clearance is between the ridge and the groove.

In some embodiments, the groove and ridge are located adjacent the first end of the internal component.

In some embodiments, the external component is a single integrally formed part or piece.

In some embodiments, the second end of the external component is configured to extend beyond a second end of the internal component.

In some embodiments, an internal surface at the second end of the external component flares outwardly and curves around the second end of the external component to an outer surface of the external component to provide a curved surface around which a portion of the tube can bend laterally.

In some embodiments, the external component comprise a shoulder at an end of the gripping region to which a user may apply an axial pushing force to the connector when fitting the connector to a coupling interface when gripping the gripping region.

In some embodiments, the external component comprise a second shoulder at an opposite end of the gripping region to which a user may apply an axial pulling force to the connector when removing the connector from a coupling interface when gripping the gripping region.

In some embodiments, the gripping region comprises one or more indents that may receive one or more fingers of a user when the user grips the gripping region.

In some embodiments, the indents have a convex or a concavely curved surface in a circumferential direction of the external component.

In some embodiments, the surface of the indent is concave in a longitudinal direction of the external component.

In some embodiments, a proximal end of the gripping region has a larger diameter than a distal end of the gripping region, the proximal end being proximal relative to the first end of the external component.

In some embodiments, a radial depth of the indents increases from the distal end to the proximal end of the gripping region.

In some embodiments, the external component comprises a cuff and an intermediate portion, the cuff being coupled to the intermediate portion to form a unitary structure or one-piece construction.

In some embodiments, the internal component comprises a groove and the cuff comprises a corresponding ridge or protrusion to rotationally couple the cuff to the internal component.

In some embodiments, the external component comprises over moulded resilient material, for example an over moulded thermoplastic elastomer, in the gripping region. The over moulding resilient material may be coloured to denote a particular size of connector.

In some embodiments a surface of the gripping region comprises a surface roughness achieved by bead blasting a surface of a forming tool to impart the surface finish to the external component in the gripping region of the external component for improved grip.

In some embodiments, the tube is a second tube and the connector is configured to connect between a first breathing tube and the second breathing tube.

In some embodiments, one of the external coupling face and the internal coupling face are configured to interact with the first tube.

In some embodiments, the second end of the connector is configured to interact with the second tube.

In some embodiments the multiple parts of the external component may be configured to be assembled prior to coupling with the internal component.

BRIEF DESCRIPTION OF THE DRAWINGS

FIG. 1 is a schematic of a respiratory assistance system.

FIG. 2 shows a perspective view of a connector according to an embodiment of the disclosed apparatus and systems.

FIGS. 5A-5B show perspective views of a component of the connector as illustrated in FIG. 2.

FIG. 6 shows a longitudinal cross-section of the component of the connector illustrated in FIGS. 5A-5B.

FIGS. 9-11 are perspective views of components of a connector as illustrated in FIG. 8.

DETAILED DESCRIPTION

Figure 3:
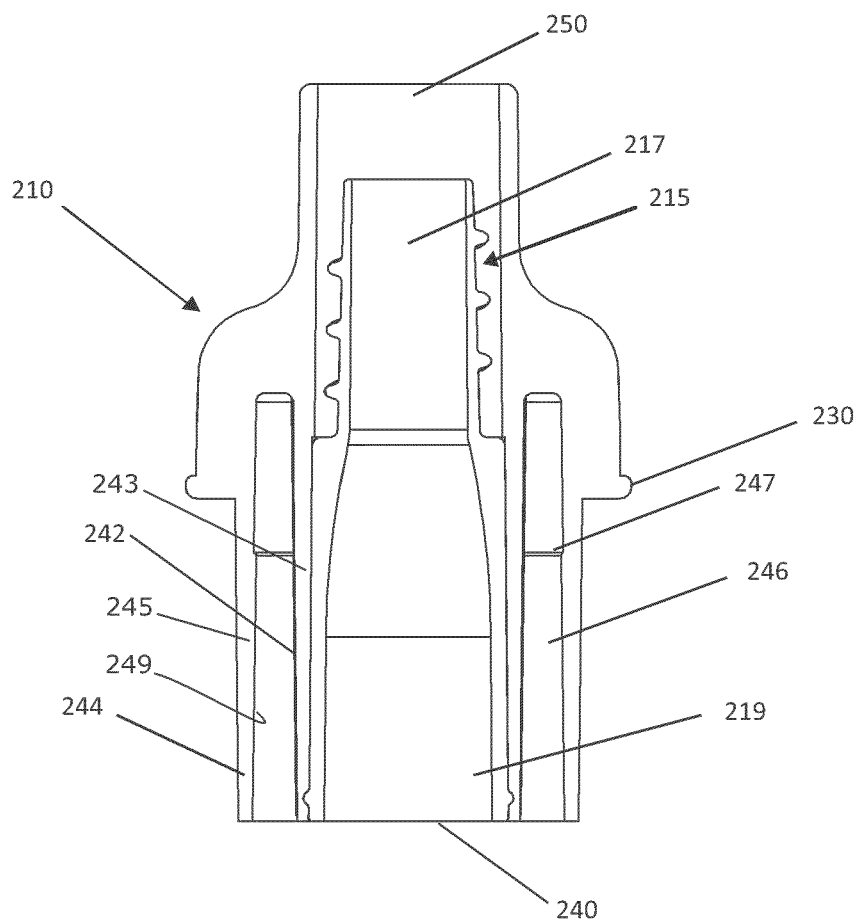
FIGS. 3-4B show a longitudinal cross-section of the connector as illustrated in FIG. 2.

A patient interface as herein described may refer to nasal interfaces (for example, nasal prongs, nasal pillows, or a nasal mask), masks (for example, an oral mask or full face mask), or invasive interfaces (for example, an endotracheal tube or tracheal mask), which may couple with a wye-piece.

FIG. 1 shows an example of a typical respiratory assistance system 100 for high flow therapy, wherein the respiratory assistance system 100 comprises a gases source 110 and a humidification apparatus 120 comprising a humidification chamber 130. The humidification apparatus 120 may be configured to heat and humidify gases supplied from the gases source 110. A medical tube 140 may transport the gases from the humidification apparatus 120 to a patient, via a patient interface 150. In some embodiments, the medical tube 140 may comprise a first and a second medical tube, wherein the second medical tube extends between the patient interface 150 and the first medical tube. In some embodiments, the second medical tube may comprise an interface tube 145. In some embodiments, the gases source 110 may form an integral part of the humidification apparatus 120.

FIG. 2 shows a coupling mechanism that couples the first and second medical tube. The coupling mechanism takes the form of a connector 200. The connector 200 may comprise multiple parts. The connector 200 comprises an external component 210 and an internal component 215, as shown in more detail in FIGS. 3-6. The external component 210 comprises a first end 240 and a second end 250, a gripping region 220, and a shoulder 230.

The first end 240 is configured to connect with a coupling interface that may be attached to the first medical tube. The second end 250 is configured to connect with the second medical tube. In the illustrated embodiment the second medical tube takes the form of the interface tube 145 (refer to FIG. 7).

The illustrated embodiment shows that the connector 200 comprises indentations and/or protrusions that define the gripping region 220 near the second end 250. The connector 200 is configured such that it forms a continuous lumen between the first and second medical tubes. In some embodiments, the first medical tube 140 may have a larger internal diameter than the second medical tube 145. In some embodiments, the connector 200 may comprise components in addition to the external component 210 and/or the internal component 215. In some embodiments, the connector 200 may comprise multiple components. For example, the gripping region 220 may be formed from a separate component and non-rotatably coupled with the external component 210, for example, via a snap-fit, adhesive, mechanical interference or welding (for example, plastic or ultrasonic welding).

Figure 7:
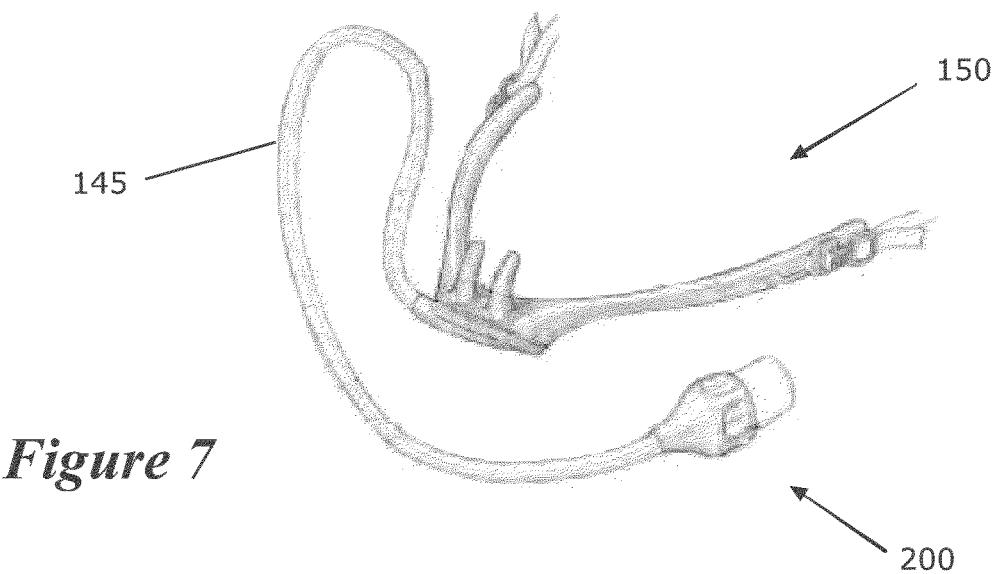
FIG. 7 shows a schematic comprising the connector illustrated in FIG. 2.

The second medical tube is configured to connect between the connector 200 and the patient interface 150 (as shown in more detail in FIG. 7). In some embodiments, it may comprise an insulated, breathable, and/or heated tube.

The first end 240 of the external component 210 comprises an internal coupling face 242, 249 and an external coupling face 244. In some embodiments the external coupling face comprises a tapered section, as seem in FIGS. 4a and 4b. The external coupling face may be referred to as the external taper 244.

The connector 200 is configured to connect with a coupling interface (not shown). The coupling interface may comprise a first coupling interface 260 configured to couple with or interact with the external coupling face 244. In some embodiments, the external coupling face seals with the first coupling interface 260 when the connector 200 is coupled with the coupling interface. The coupling interface may comprise a second coupling interface 262 configured to couple with or interact with the internal coupling face 242, 249, for example, via a snap-fit.

In some embodiments the external coupling face 244 is an outer surface of an outer wall 245 of the external component 210. In some embodiments the internal coupling face 242 is an outer surface of an inner wall 243 of the external component. In some embodiments the internal coupling face may be an inner surface 249 of the outer wall 245 of the external component. In some embodiments the internal and external walls 243, 245 are concentric. In some embodiments, the internal coupling face 242 or 249 seals with the second coupling interface 262 when the connector 200 is coupled with the coupling interface. In some embodiments the external component may comprise two internal coupling faces 242, 249, such that the second coupling interface 262 seals with both of the internal coupling faces 242, 262 of the external component when the connector 200 is coupled with the coupling interface.

Figure 4A:
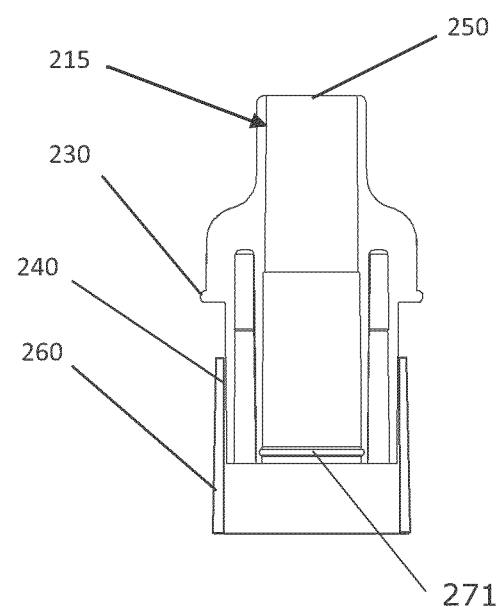
Figure 4B:
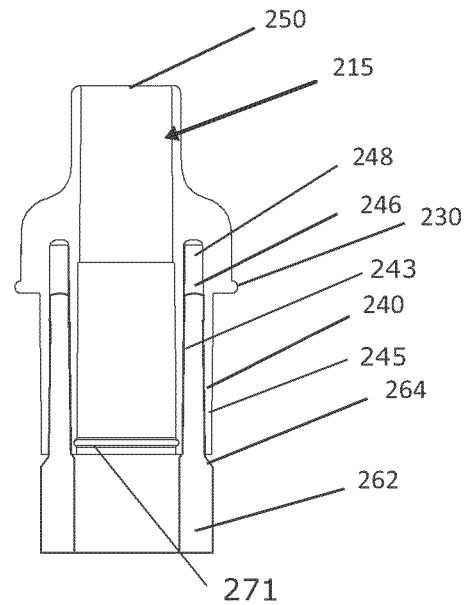

The coupling may be configured to create a gases path between the connector 200 and the first medical tube, or between the connector 200 and the second medical tube, such that the gases can be delivered to the patient interface 150. The first coupling interface 260 may, for example, refer to a 22 mm tapered female connection, as shown in FIG. 4A. The second coupling interface 262 may, for example, refer to a proprietary male connection, as shown in FIG. 4B. Thus, the connector 200 is configured to comprise different coupling interfaces, which improves the usability of the connector 200.

In an embodiment, the internal coupling face 242, 249 may comprise a taper or tapered section, such that the connector 200 comprises dual tapers 242, 244 or dual tapered sections. The dual tapers or dual tapered sections can be co-axial and parallel to each other.

The first coupling interface 260 may comprise a different detachment mechanism to the second coupling interface 262. A user may rotate the connector 200 when coupled with the first coupling interface 260 to break the taper before pulling the components apart. The user applies a torque to the connector 200 to overcome the coupling force between the connector and the first coupling interface 260, and break the taper i.e. break the press fit between the external taper 244 and the first coupling interface 260. Once the taper has been broken (i.e. the coupling force has been overcome), less force or a reduced force is required to pull or detach the components, than if the user was to simply pull the components apart in an axial direction without first breaking the taper.

Alternatively, to disconnect the second coupling interface 262, the user may pull the component apart in an axial direction. The shoulder 230 may aid in providing a region for a user to apply an axial pulling force to the connector 200. The shoulder 230 provides a portion the user can grip or gain purchase on to apply the axial pulling force to the connector 200. The shoulder 230 may aid in providing a region for a user to apply an axial pushing force to the connector 200 when fitting the connector to a coupling interface.

The connector 200 is configured to provide a sufficient surface for the user to grip while pulling the components apart and also provide a surface that enables rotation of the connector 200 to break the connection. By way of example, at least a portion of the connector 200 is designed to meet a medical taper as defined by ISO5356-1:2004. The connector 200 comprises an external component 210 rotatably coupled to the internal component 215. The internal component 215 rotates independently of the external component 210. The external component 210 may comprise a single part that integrates the gripping region 220 with the external taper 244. The external component 210 rotates as the user applies a rotational force onto the gripping region 220, since the gripping region 220 is integrally formed with the external taper 244 to provide a unitary structure. Use of a single part or unitary structure may be advantageous, as it may be lightweight and easier to manufacture than a multi-part assembly.

Referring again to FIG. 3, the external component 210 comprises a cavity 246 that extends either side of the internal coupling face 242. The cavity 246 is defined by the internal coupling face 242 and the external coupling face (i.e. the external taper 244). The second coupling interface 262 may insert into the cavity 246 during connection (as shown in FIG. 4B). In some embodiments, upon coupling of the internal coupling face 242 and the second coupling interface 262, a portion of the cavity 246 referred to as recess 248 may remain unfilled. The recess 248 reduces the weight of the connector 200 and may reduce manufacturing time. The recesses 248 may also reduce or eliminate formation of sink marks by reducing shrinkage during manufacturing.

In some embodiments, the second coupling interface 262 may comprise a ledge 264 to limit the distance the second coupling interface 262 extends into the cavity 246. Alternatively the ledge 264 limits the distance the connector 200 extends over the second coupling interface 262. In some embodiments, the connector 200 may couple with the ledge 264, for example, via a clipping mechanism.

A groove or shoulder 247 may be disposed on a wall of the external component. In the illustrated embodiment a shoulder 247 is disposed on the inner surface 249 of the outer wall 245 of external component such that it may correspond with a protrusion on the second coupling interface 262 to enable a snap-fit connection between the second coupling interface 262 and the internal coupling face 249. Alternatively or additionally a shoulder may be provided on the outer surface 242 of the inner wall 243 of the external component such that it may correspond with a protrusion on the second coupling interface 262 to enable a snap-fit connection between the second coupling interface 262 and the internal coupling face.

The first coupling interface 260 forms a connection with the external taper 244. The external taper 244 is inserted into the first coupling interface 260. A user may insert the external taper 244 to a desired level. The shoulder 230 can function as an insertion limit, and limit the length the external taper 244 is inserted into the first coupling interface.

The gripping region 220 comprises indentations and/or protrusions that form at least a partially uneven surface to improve the grip. The gripping region 220 is designed to be comfortable in use. In some embodiments, the indentations and/or protrusions are contoured to correspond to or represent the shape of fingers to improve user comfort and to allow the user to have a more secured grip. The uneven surface may provide a visual indicator of the gripping region 220 to the user. In some embodiments, the gripping region 220 may comprise a different colour and/or texture that enable distinction between different regions of the external component 210. In some embodiments, colour or different coloured regions may be used to provide the user with a visual indication of the location of the gripping region 220, making it intuitive for the user to grip the connector 200 within the gripping region 220.

In some embodiments, the gripping region 220 is partially opaque in comparison with other regions of the external component 210, such as, for example, the first and second ends 240, 250, respectively, that may be translucent. This provides a visual indication to the user to grip the connector 200 in this region, thereby distinguishing between different regions of the external component 210. The texture of the gripping region 220 may be configured to be rougher than other regions of the external component 210. In some embodiments, the texture may be designed to increase the friction of the gripping region 220 such that the user can more easily grip the connector 200.

The gripping region 220 is configured such that the user may apply multiple gripping actions without the fingers slipping, for example, a circular grip for the application of torque. In some embodiments, the shoulder 230 may provide an alternative or additional region for the user to grip and apply force to the connector 200 for disconnection.

FIGS. 5-6 describe the internal component 215 in further detail. The internal component 215 is configured to be received within the external component 210. A proximal end 219 and a distal end 217 of the internal component 215 may correspond with the first end 240 and the second end 250 of the external component 210, respectively, wherein the proximal end 219 as herein described may refer to the end nearest to the gases source and/or humidification apparatus in use. Similarly, the distal end 217 as herein described may refer to the end nearest to the patient in use. A ridge 270 is positioned at the proximal end 219. The ridge 270 is configured to couple with a corresponding groove in the first end 240 of the external component 210, for example, via a snap-fit, for example groove 271 shown in FIGS. 4A and 4B. As a result, the internal component 215 is coupled with the external component 210. The internal component 215 is rotatably coupled with the external component 210, such that the internal component 215 can rotate relative to the external component 210.

In some embodiments, the ridge 270 may be an annular ring while, in other embodiments, the ridge 270 may comprise discrete protrusions configured to couple with the external component 210. The coupling may form a sufficient pneumatic seal between the internal component 215 and the external component 210. For example a sealing component (e.g. an o-ring) may be fitted between the internal and external components, or a clearance between the internal and external components may be sufficient to allow for relative rotation there between, yet be sufficiently tight such that at operating pressures any leakage between the internal and external components is negligible or insignificant during use. A clearance between the internal and external component combined with a length of the internal and external components over which the components fit together result in negligible or insignificant leakage of respiratory gases between the external and internal components at operating pressures. A clearance between the ridge 270 and groove 271 may allow relative rotation between the components while being sufficiently close to provide for insignificant or negligible leakage of gases between the components. In some embodiments the groove and ridge are located adjacent to the first end of the internal component so that leakage between the components is reduced. A pneumatic seal can be created between the external component and the coupling interface 260, 262.

The internal component 215 may be rotatably coupled to enable the second medical tube to rotate or swivel independently from the external component 210. This decreases the likelihood of the second medical tube becoming tangled or twisted in response to patient movement and/or during setup. Thus, the internal component 215 moves with relation to patient movement and accounts for the patient's movement. This may increase patient comfort and acceptance of the therapy.

An attachment mechanism 280 may be located at an attachment region 285 near the distal end 217 of the internal component 215. The attachment region 285 may have a different diameter when compared with other sections of the internal component 215. In the illustrated embodiment the diameter of the attachment region 285 may be smaller when compared with other sections of the internal component. Alternatively the diameter of the attachment region may be the same as the diameter of the internal component 215. The attachment mechanism 280 facilitates attachment of the second medical tube to the internal component 215. In some embodiments, the attachment mechanism 280 comprises a thread onto which the second medical tube may be wound. The second medical tube may not easily be removed from the attachment mechanism 280 in use, due to the rotatable characteristics of the internal component 215 with respect to the external component 210. Thus, the attachment mechanism 280 reduces accidental detachment of the second medical tube. A pneumatic seal can be created between the medical tube and the attachment mechanism 280 of the internal component 215.

In some embodiments, the attachment region 285 may comprise a longitudinal taper. Thus, the attachment region 285 near the distal end 217 of the internal component 215 has a smaller diameter than the attachment region 285 nearer to the proximal end 219 of the internal component 215. The diameter nearer to the proximal end 219 of the internal component 215 may be larger than the internal diameter of the second medical tube. As a result, the second medical tube is at least partially stretched such that it applies an inward force to the attachment mechanism 280. Thus, the second medical tube holds or couples tightly to the attachment region 285 of the internal component 215. This assists in maintaining the attachment between the second medical tube and the internal component 215 and may improve the retention force for the second medical tube. The second medical tube is unlikely to become unscrewed from the attachment region 285 of the internal component 215 due to the way the second medical tube is attached to the attachment region 285. Use of an attachment mechanism, such as a thread, provides a consistent and repeatable manufacturing solution.

In an embodiment, an adhesive may be used to attach the second medical tube to the attachment region 285. The use of adhesive provides a simple and cost effective attachment procedure. In some embodiments, a collar may be used to hold the second medical tube onto the attachment region 285 of the internal component 215. The collar may be substantially rigid. In some embodiments, the collar may be substantially flexible or may comprise a combination of rigid and flexible portions. The collar is configured such that it extends over the outer surface of the second medical tube and secures the second medical tube onto the attachment region 285 of the internal component 215. In some embodiments, the thread is disposed on the inner wall of the external component 210 such that it may engage with the outside of the second medical tube. In some embodiments, projections and/or keying may exist, which may enable the second medical tube to be securely attached to the internal component 215. A latch or locking mechanism may also be used to hold the second medical tube in place.

In some embodiments, the internal component 215 comprises different colours to aid with size distinction. The external component 210 may be translucent (e.g. transparent or semi transparent) such that the colour or colours of the internal component 215 may be visible. This allows a user to determine the correct sizing to use based on the shade, pattern, and/or colour of the internal component. For example, the internal component 215 may be blue to indicate a large size, red to indicate a medium size, and yellow to indicate a small size. Another example may comprise a dark green to indicate a large size with progressively lighter greens indicating medium and small sizes respectively. These examples are intended to be illustrative only and should in no way limit the embodiments described to a specific colour and/or sizing regime.

Sufficient space exists between the internal component 215 and the external component 210 to allow the second medical tube to expand in use. In some embodiments, for example, the second medical tube may heat up and/or take up liquid condensate and, thus, space between the internal component 215 and the external component 210 allows for any expansion of the second medical tube. In some embodiments, expansion may occur without causing the second medical tube to contact the inner wall of the external component 210. As a result, condensate may continue to be removed from the second medical tube and, thus, the breathability characteristics of the second medical tube remain unimpaired. Also, by reducing or eliminating the likelihood of the second medical tube contacting the inner wall of the external component 210, even on expansion of the second medical tube, allows the second medical tube to continue to swivel or rotate freely.

FIG. 6 illustrates the flow path that gases may take as they travel from the first medical tube, through the connector 200, and into the second medical tube. The internal lumen of the connector 200 and/or the coupling between the internal component 215 and the second medical tube is designed to be streamlined. The internal lumen is smooth to reduce the resistance to flow in the system. A wall section ($W_S$) within the attachment region 285 of the internal component 215 is chosen such that it does not substantially reduce the diameter of the flow path of the gases. An increased wall section ($W_S$) thickness increases the robustness of the attachment region 285, however may contribute to an increased resistance to flow. Decreasing the wall section ($W_S$) thickness may reduce resistance to flow but also decreases the overall strength and may render the connector 200 vulnerable to damage and more fragile to manufacture processes. Thus, the thickness is optimised to form the connector 200 such that the attachment region 285 is sufficiently robust without impacting substantially on resistance to flow. In some embodiments, the wall section ($W_S$) may be between 0.2 mm to 1 mm thick. In some embodiments, the wall section ($W_S$) may be 0.5 mm thick. Thus, the resistance to flow may not significantly increase as the gases pass from the first to the second medical tube via the connector 200.

FIG. 7 shows the connector 200 as part of a system comprising the patient interface 150 and the interface tube 145. The patient interface 150 shown in FIG. 7 is for example purposes only and is in no way limiting. The patient interface shown in this illustrated embodiment is a non-sealing nasal cannula that can be used in a high flow therapy delivery mode. Alternative patient interfaces can also use the interface tube and connector of the present disclosure in order to couple the interface tube and patient interface, to the medical tube to supply breathing gases to the user via the patient interface and interface tube. Some examples of other patient interfaces include: nasal pillows, nasal masks, full face masks, vented and non vented masks, nasal plugs, oral masks and tracheal interfaces. Advantageously, the swivel connector allows for a medical breathing tube to rotatably swivel and therefore to avoid unnecessary torsion or other forces, including entanglement of such a tube when such a tube is twisted or rearranged by a user. In addition, the external component being independent of the swivel part allows a user to more easily apply a torque or twist to the external component and thereby improve useability for breaking of a connection when connected to another connector. The ability to more easily break the connection facilitates the disconnection of a pneumatic seal that is otherwise formed by the coupler.

Figure 8:
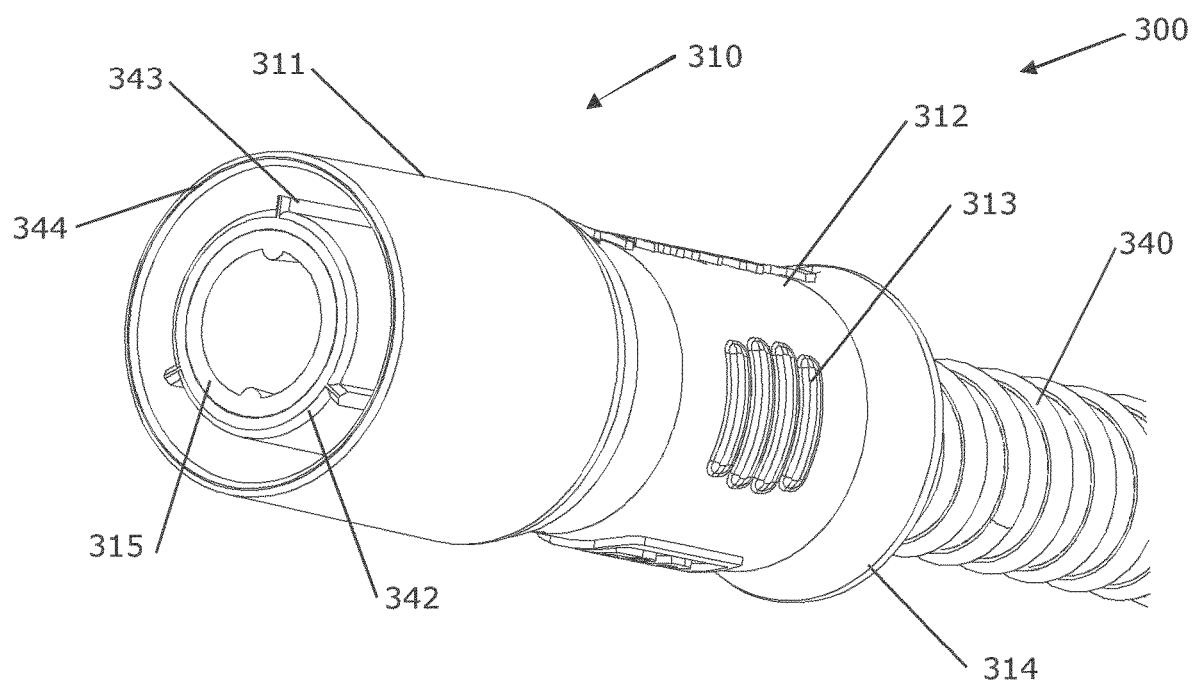
FIG. 8 is a perspective view of a component of a connector according to an embodiment of the disclosed apparatus and systems.

FIGS. 8-11 illustrate an embodiment that comprises a connector 300 configured to couple with a medical tube 340. The medical tube 340 may be an interface tube, e.g. tube 145 of FIG. 1. The connector 300 comprises an external component 310 and an internal component 315. FIG. 8 also shows an alternative embodiment of a coupler that includes an external component that is formed from multiple parts. These multiple parts are connected together to form a unitary structure or act like a unitary structure due to the permanent nature of the coupling. The coupling can be a permanent clip connection, a permanent snap fit or a permanent press fit. Alternatively the parts are removably coupled, but the coupling is rigid enough that the external component behaves as a unitary structure.

In the illustrated embodiment, the external component 310 comprises a plurality of parts that together form the external component 310. In the illustrated embodiment the external component 310 comprises a cuff 311 and an intermediate component 312. The medical tube 340 may be configured to couple with the internal component 315, forming an internal assembly. The internal component 315 and the medical tube 340 are configured to be received by the external component 310.

FIG. 9 illustrates the internal component 315 in more detail. The internal component 315 comprises an attachment mechanism 380 configured to attach to the medical tube 340. The attachment mechanism 380 may in some embodiments take the form of a thread, an adhesive or a latch. In the illustrated embodiment the attachment mechanism 380 is a thread. The attachment mechanism 380 is configured to attach to the inner surface of the medical tube 340 via the outer surface of the internal component 315. In an embodiment, the attachment mechanism 380 may be configured to attach to the outer surface of the medical tube 340 via the inner surface of the internal component 315.

The internal component 315 may comprise a first region 317 and a second region 319. The second region 319 comprises the attachment mechanism 380. The first region 317 comprises a groove 320 configured to rotatably engage with a protrusion 322 on the cuff 311 as shown in more detail in FIG. 10B. In an embodiment, multiple protrusions 322 engage with the groove 320. In an embodiment, the protrusion 322 extends around the entire perimeter of the cuff 311.

The internal component may comprise a wall 321. The wall 321 may define a side or side wall of the groove 320. The wall 321 extends outwardly from the body of the internal component. The wall 321 extends around the perimeter of the internal component 315. The wall 321 defines the transition between the first region 317 and second region 319. In an embodiment, the wall 321 may define a bearing surface for the cuff 311 wherein a portion of the cuff can bear against the wall 321 in use.

The protrusion 322 of the cuff 311 may be a wedge or post. This enables a snap-fit connection to be formed between the external component 310 and the internal component 315. The protrusion 322 is configured to allow the internal component 315 to be rotatably coupled with the external component 310, such that the internal component 315 can rotate relative to the external component 310. Rotatable coupling between the internal component 315 and the external component 310 reduces or eliminates the likelihood of the medical tube 340 being detached or removed from the attachment mechanism 380 of the internal component 315. The rotatable internal component 315 also compensates for patient movements, which in turn cause the medical tube 340 to move. The rotatable internal component 315 provides the same or similar advantages as the rotatable inner component 215, described with respect to FIGS. 3 to 6.

A clearance may be formed between the internal component 315 and the external component 310. This further facilitates rotatable coupling between the internal component 315 and the external component 310. In an embodiment, the surfaces of the internal component 315 and the external component 310 may be semi-contacting surfaces to facilitate the rotational ability of the coupling. In an embodiment, the rotatable coupling between the internal component 315 and the external component 310 may utilise a different mechanism, for example, a mechanical bearing to promote or facilitate rotation.

The medical tube 340 is configured to non-rotatably couple with the internal component 315. Thus, patient movement or rotation of the medical tube 340 causes the internal component 315 to rotate or swivel. As the internal component 315 can rotate or swivel relative to the external component 310, this movement is not translated to the external component 310. As a result, the flexibility of the system is improved over prior systems and makes the currently described connector embodiments more advantageous for use over prior systems.

In some embodiments the second region 319 comprises a taper. For example, the diameter at the proximal end of the second region 319 is larger than the diameter at the distal end of the second region 319. Proximal in this case refers to the end of the second region 319 of the internal component 315 which is nearest to the first region 317. Distal in this case refers to the end of the second region 319 of the internal component 315 that is configured to interact with the medical tube 340. The taper reduces or eliminates the likelihood of the medical tube 340 detaching or being removed from the internal component 315.

A ledge or shoulder 385 is disposed on the internal component. The ledge 385 acts as a stopper to the medical tube 340 as it is attached to the internal component 340 via the attachment mechanism 380. This prevents the medical tube 340 from being inserted too far onto the internal component 315. As a result, the medical tube 340 may be sufficiently inserted onto the second region 319 of the internal component 315, without being moved onto the first region 317.

The second region 319 of the internal component 315 comprises an end which forms a pneumatic connection between the medical tube 340 and a component of the respiratory assistance system 100. For example, the medical tube 340 pneumatically connects with a different medical tube, such that the respiratory assistance system 100 provides conditioned gases to the patient.

In some embodiments, the internal component 315 may comprise multiple parts. The multiple parts may couple together, for example, using a snap-fit mechanism, latching, or adhesives.

The external component 310 comprises a cuff 311 and an intermediate component 312. FIGS. 8, 10A-10B describe the cuff 311 in more detail. The cuff 311 defines a first end of the external component 310. The intermediate component 312 defines a second end of the external component 310. As discussed, the cuff 311 comprises a coupling mechanism such as a protrusion 322 to form a rotatable connection with the internal component 315. The cuff 311 further comprises a dual coupling system. The dual coupling system comprises an internal coupling face 342 and an external taper 344. The internal coupling face 342 is configured to couple with a proprietary male connector. The external taper 344 is configured to couple with a 22 mm female taper. Thus, the dual coupling system improves the flexibility of the respiratory assistance system 100 to couple with different medical tubes as required.

The internal coupling face 342 comprises at least one rib 343 to interact with at least one corresponding groove on the proprietary male connector to aid with alignment during coupling. In the illustrated embodiment the internal coupling face comprises three ribs extending longitudinally along the internal coupling face 342. The ribs are equally spaced around the perimeter of the internal coupling face 342. Alternatively the ribs can be positioned at any predetermined distance or angle relative to each other. Further in some alternative embodiments the ribs 343 may extend in an arcuate path along the internal coupling face 342. One example is a twisted path, or an S shaped path. The rib arrangement described above can also be implemented in the connector embodiment described with reference to FIGS. 1 to 6. The ribs would be disposed on the internal coupling surface 242, and extend longitudinally along the internal coupling surface 242.

In some embodiments, the internal coupling face 342 may comprise at least one groove configured to align with at least one corresponding rib on the proprietary male connector. In some embodiments, a tapered surface or protrusions may be used to facilitate alignment between the components.

The cuff 311 comprises a coupling mechanism 350 to facilitate engagement between the cuff 311 and the intermediate component 312. The coupling mechanism 350 facilitates a snap-fit connection between the cuff 311 and the intermediate component 312. The snap-fit connection may be formed using a clipping mechanism or a latch or other suitable mechanisms. In some embodiments the connection between the cuff 311 and the intermediate component 312 can be coupled using, adhesives, mechanical interference or welding (for example, plastic or ultrasonic welding) or any other suitable permanent attachment mechanism.

Figure 11:
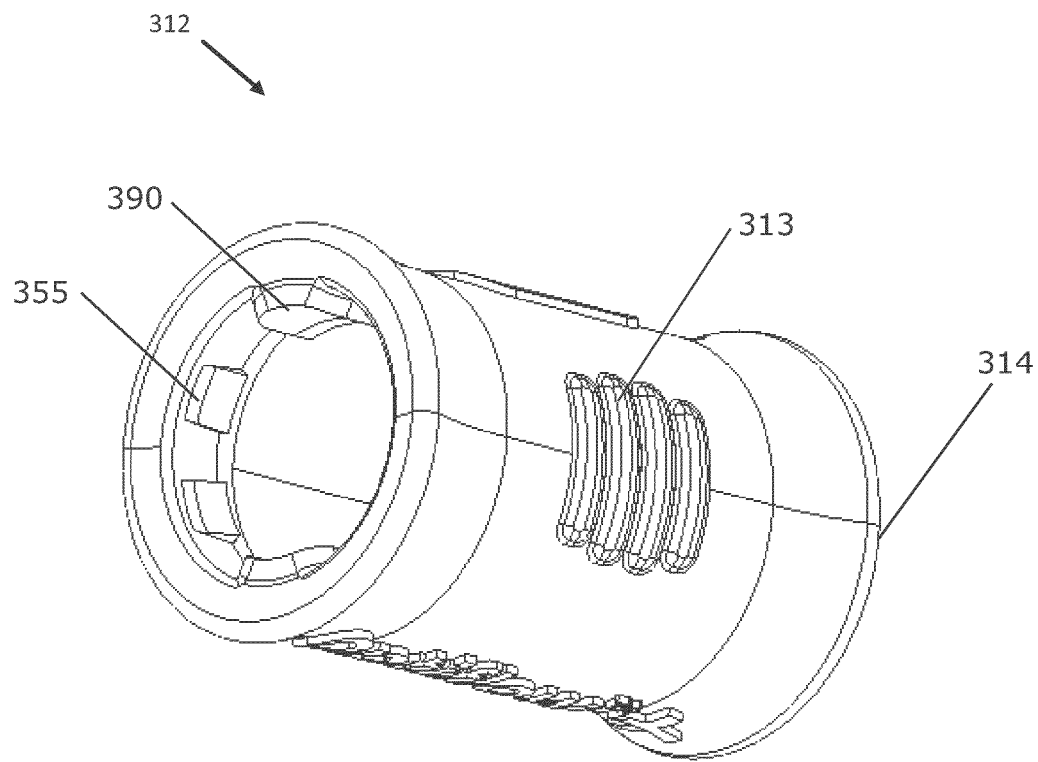

FIGS. 10A-11 illustrate an embodiment wherein the cuff 311 is configured to receive clips 355 from the intermediate component 312. In some embodiments, the coupling mechanism 350 comprises apertures 353 that are configured to receive corresponding clips 355 on the intermediate component 312. In some embodiments the cuff 311 may comprise a single aperture 353 configured to receive a single clip 355. In the illustrated embodiment, the cuff 311 comprises multiple apertures 353, configured to receive multiple clips 355.

In an embodiment, the cuff 311 may comprise a single clip configured to be received by a single aperture disposed on the intermediate component 312. In an embodiment, the cuff 311 may comprise multiple clips, configured to be received by multiple apertures on the intermediate component 312.

In some embodiments, the aperture may extend at least partially around the cuff 311. In some embodiments, the clip may extend at least partially around the cuff 311. In some embodiments, a single aperture may be configured to receive multiple clips.

The coupling mechanism 350 is configured to form a non-rotatable coupling between the cuff 311 and the intermediate component 312. In some embodiments the cuff 311 is permanently coupled to the intermediate component 312. In some embodiments, the cuff 311 may be removably coupled to the intermediate component 312.

The intermediate component 312 comprises a protuberance 390 that mates with a corresponding recess in the cuff 311 to aid in the alignment of the intermediate component 312 and the cuff 311 during manufacturing.

In an embodiment, the intermediate component 312 may comprise a recess that aligns with a corresponding protuberance in the cuff 311. In an embodiment, a plurality of protuberances 390 are disposed on the intermediate component 312. The plurality of protuberances 390 correspond with a plurality of the recesses 395 on the cuff 311. For example, the intermediate component 312 may comprise two of the protuberance 390 that may mate with two of the recess 395 of the cuff 311. In an embodiment, the intermediate component 312 may comprise multiple recesses that may align with multiple corresponding protuberances on the cuff 311.

The protuberance 390 comprises a shape that aids or facilitates mating with the recess 395. The protuberance 390 may be circular, oval or rectangular. Other shapes also fall within the scope of the disclosed apparatus and systems.

The intermediate component 312 comprises grips 313 to aid the user when connecting or disconnecting the connector 300. The grips 313 are any suitable features that promote grips. For example the grips 313 can be in the form of ridges, protrusions, a textured surface, indentations for a user to insert a finger, or may comprise different materials. The grips 313 are positioned on each side of the intermediate component 312. In an embodiment, a single grip 313 may be used on a single side of the intermediate component 312. In an embodiment, multiple of the grips 313 are disposed on the intermediate component, and the surface of the intermediate component 312 may comprise multiple regions of the grips 313.

In some embodiments, the internal component 315 extends within the external component 310 to the dual coupling system of the cuff 311. In some embodiments, the intermediate component 312 comprises a first end and a second end, wherein the first end is configured to couple with the cuff 311, and the second end is configured to receive the internal part 315. In some embodiments, the second end of the intermediate component 312 may extend beyond the internal component 315, once the internal component 315 has been inserted into the external component 310.

The second end of the intermediate component 312, that is configured to extend beyond the internal component 315, comprises a smooth surface 314. The smooth surface 314 is rounded or contoured. The surface 314 reduces or eliminates damage to the medical tube 340 caused by the intermediate component 312. The surface 314 also protects the medical tube 340 from the internal component 315. As a result, the medical tube 340 may endure acute bending with reduced damage to the medical tube 340.

The medical tube 340 is coupled with the internal component 315 forming the internal assembly, prior to assembly with the external component 310. The cuff 311 and the intermediate component 312 may be assembled together prior to the insertion of the internal assembly. In some embodiments, the cuff 311 may be coupled with the internal assembly, and the intermediate component 312 may be inserted onto this assembly. In some embodiments, the internal assembly may slidingly engage with the external component 310. In some embodiments, the intermediate component 312 may be coupled with the internal assembly, following which the cuff 311 may be coupled with the assembly.

The cuff 311 is non-rotatably coupled to the intermediate component 312. As a result, any force applied to the cuff 311 will cause both the cuff 311 and the intermediate component 312 to move together. Non-rotatable coupling enables a user to break the connection with the coupling interface by applying a twisting motion or a torque to the external component 310, before removing the connector 300. The internal component 315 is rotatably coupled to the external component 310, to enable the medical tube 340 to move and rotate freely within the connector 300. The internal component 315 is rotatable relative to the external component 310, and also allows the medical tube to rotate relative to the external component 310.

The cuff 311 and the intermediate component 312 are formed from a rigid or semi-rigid material. In some embodiments, the cuff 311 and the intermediate component 312 may be formed from different materials to each other.

In an embodiment, the external component 310 may comprise a single part. In some embodiments, the external component 310 may comprise multiple parts.

Figure 12:
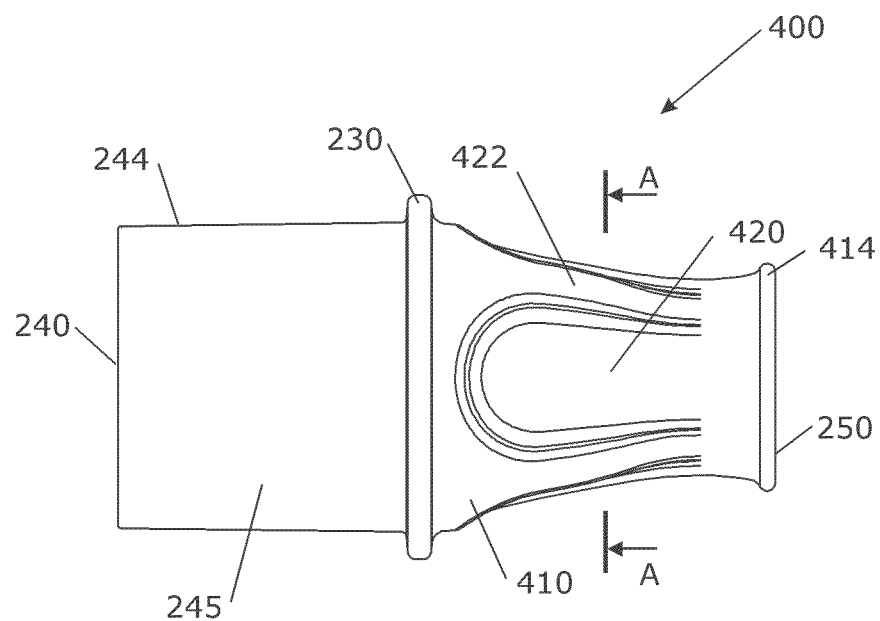
FIG. 12 shows a side view of a connector according to one embodiment.

A further connector embodiment is illustrated in FIG. 12. The connector comprises an external component 410, illustrated in FIGS. 12 to 16. The external component 410 forms the connector 400 together with the internal component 215 illustrated in FIGS. 5A to 6, as described with reference to FIGS. 2 to 7 (not shown in FIGS. 12 to 16). The external component 410 is a single integrally formed part or piece, and has some features similar to the single integrally formed external component 210 described above. External component 410 is illustrated as having ribs 443 to interact with at least one corresponding groove on a proprietary male connector to aid with alignment during coupling, similar to ribs 343 described above with reference to external component 310. A second end 250 of the external component 410 is configured to extend beyond a second end of the internal component 315. The second end 250 comprises a smooth surface 414. The smooth surface 414 is rounded or curved, to reduce or eliminate damage to the medical tube attached to the internal component. Surface 414 comprises an internal surface that faces an outer surface of the tube attached to the internal component 215. The internal surface flares outwardly at the second end of the external component. Surface 414 also extends around the second end of the external component, such that the second end is rounded at least at an internal bore of the external connector in which the internal component is received. Where the tube is bent laterally to a side of the connector, the tube wraps around the curved surface and the rounded end of the connector which prevents or reduces kinking and damage to the tube. The surface 414 also protects the medical tube (e.g. tube 340) from the internal component 315. As a result, the medical tube may endure acute bending with reduced damage to the medical tube. Other features of the external component 410 that are the same or similar to features of external component 210 are indicated with the same reference numerals from FIGS. 2 to 4B.

In some embodiments the external component 410 comprises a shoulder 230 to which a user may apply an axial pushing force to the connector when fitting the connector to a coupling interface while gripping a gripping region 420 of the connector. The shoulder 230 may be provided at a proximal end of the gripping region 420 (being proximal to the first end of the connector that interfaces to a coupling interface). In some embodiments, the external part 410 may comprise a second shoulder 430 to which a user may apply an axial pulling force to remove the connector from a coupling interface while gripping the gripping region 420. The second shoulder 430 may be provided at an opposite distal end of the gripping region 420. In other words, the griping region 420 may be provided between a first shoulder 230 and a second shoulder 420, the first and second shoulders providing a region for a user to apply pushing and pulling axial forces to connect and disconnect the connector to and from a coupling interface while gripping the gripping region 420.

Figure 16:
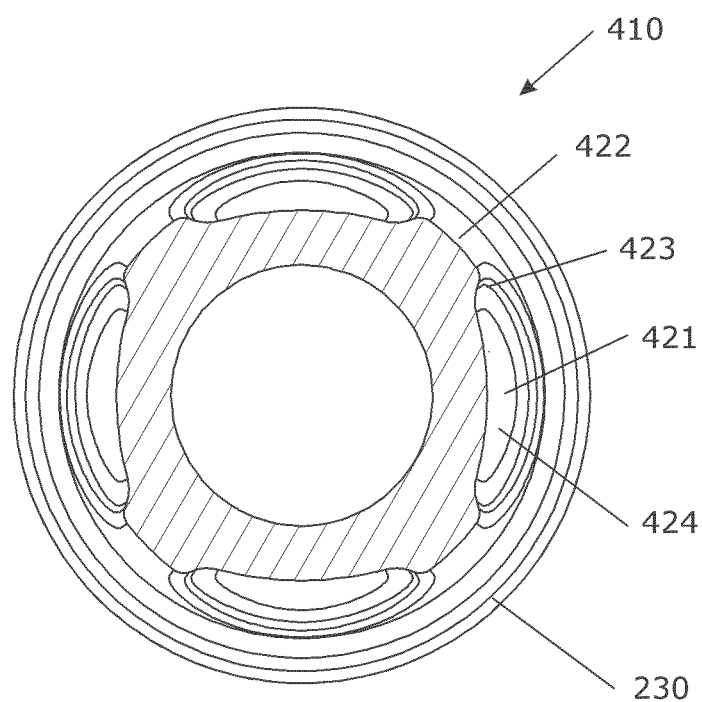
FIG. 16 is a cross sectional view of the external component shown in FIG. 13, the cross section being on line AA shown in FIG. 12.

The gripping region 420 provides finger grips to allow a user to provide torque to the external component, to rotate or twist the connector when connecting or disconnecting the connector to or from a coupling interface. The gripping region 420 comprises one or more indents 421 that may receive one or more fingers of a user when the user grips the gripping region. The indents provide raised portions 422 against which a user may apply lateral forces to turn the external part of the connector on an axis of the connector. In some embodiments, the indents may be substantially concave in shape and include a rounded section, as described with reference to external component 210 of FIG. 2. In some embodiments, as best shown in FIG. 16, the indents may have a convex curved surface 424 when viewed from an end of the connector, or may have a concavely curved surface. In other words each indent may have a surface 424 curving outwardly between longitudinal sides 423 of the indent. As shown, in some embodiments the proximal end of the gripping region has a larger diameter than a distal end of the gripping region. The surface 424 of the indent may be concave in a longitudinal direction. Thus, in some embodiments the surface of each indent may have a convex curved profile in a circumferential direction of the external component and a concave curved profile in a longitudinal direction. The surface of each indent may be described as a hyperbolic paraboloid (or a saddle shape) that curves inwards in a longitudinal direction and outwards in a circumferential direction. A benefit of such a shaped surface for the indents in that the wall thickness of the external part is more constant, compared to form example the embodiment of FIG. 2. Having a more constant cross section may assist with manufacture of the external component, for example with a moulding process of the connector.

Figure 13:
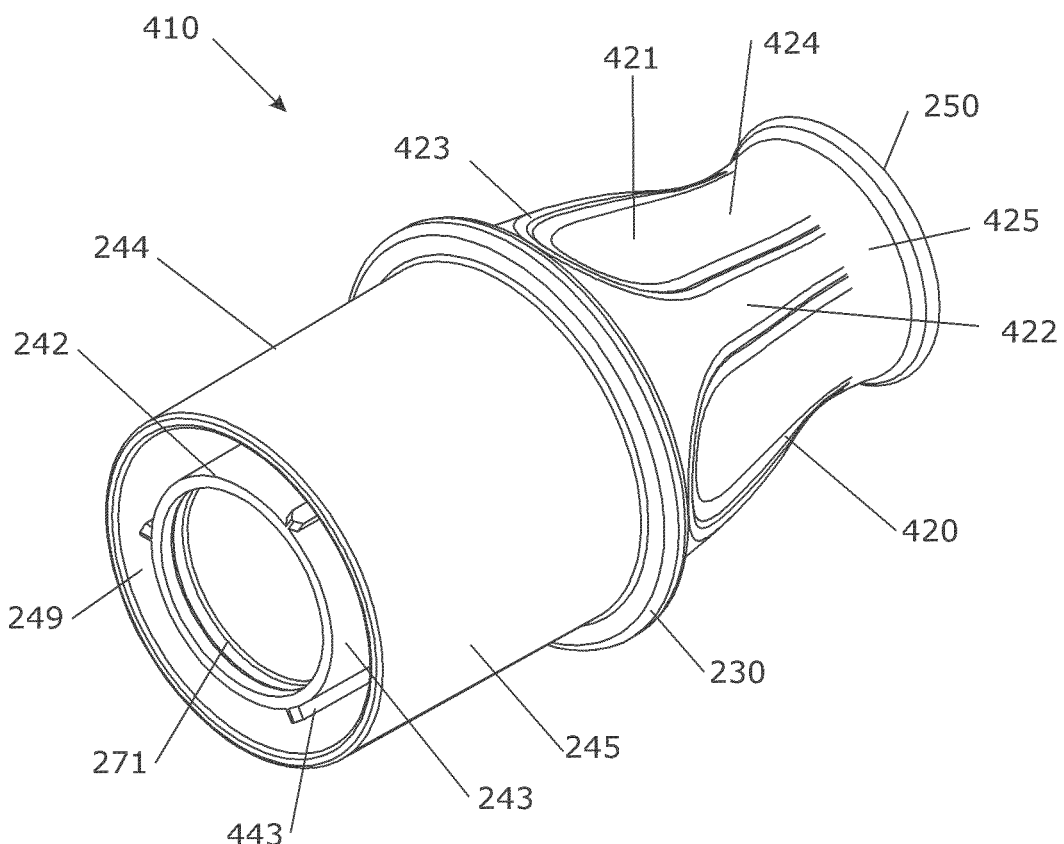
FIG. 13 is a perspective view of an external component of the connector of FIG. 12.
Figure 14:
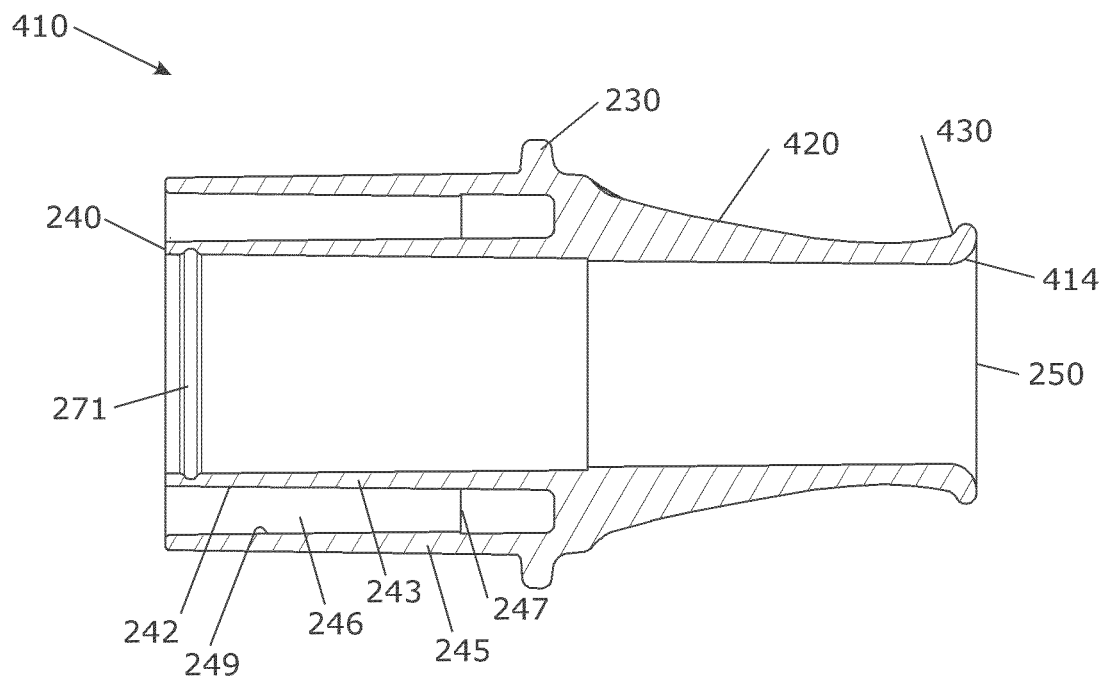
FIG. 14 is a cross sectional view of the external component shown in FIG. 13 along a longitudinal centreline of the component.
Figure 15:
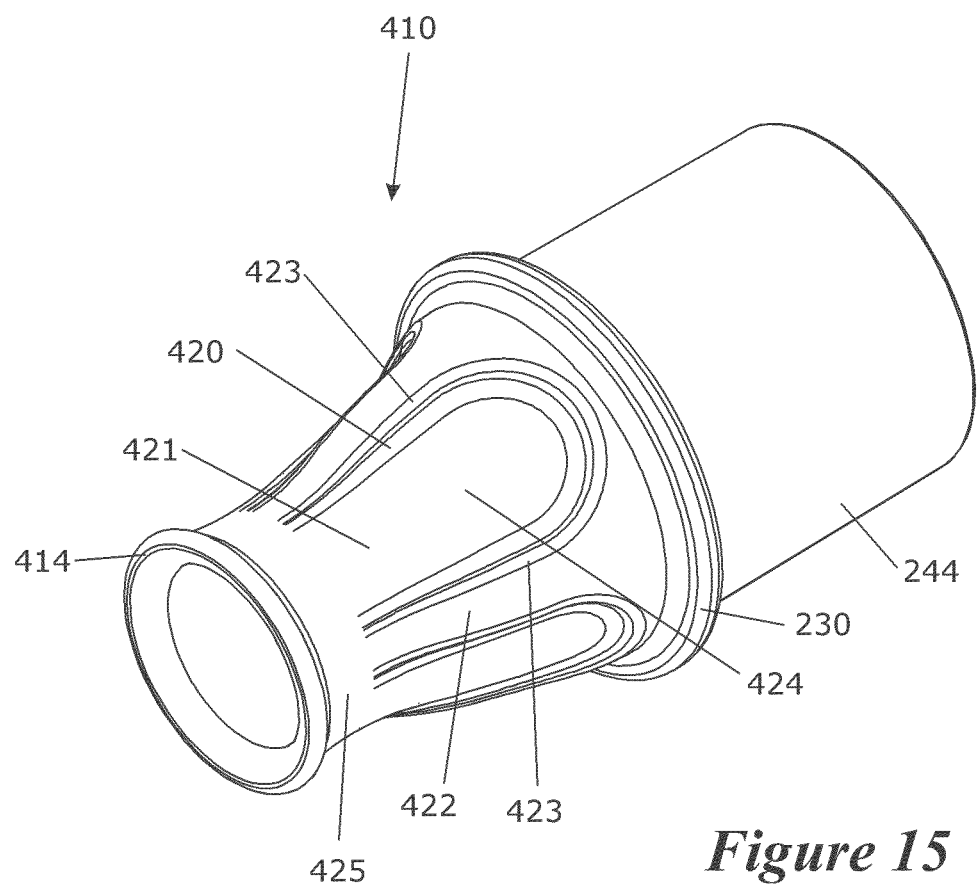
FIG. 15 is a perspective view of the external component of FIG. 13 viewed from an opposite end of the component.

In some embodiments a radial depth of the indents increases from the smaller diameter end of the gripping region to the larger diameter end of the gripping region, as shown in FIGS. 13 and 15. At the smaller diameter end of the gripping region the indents taper out such that the gripping region has an annular portion 425 at the distal end without indents. The annular portion 425 is adjacent to the shoulder or rim 430 of the external connector.

As described above, in some embodiments the gripping region 420 is partially opaque in comparison with other regions of the external component 410, such as, for example, the first and second ends 240, 250, respectively, that may be translucent. This provides a visual indication to the user to grip the connector 400 in this region, thereby distinguishing between different regions of the external component 410. The texture of the gripping region 420 may be configured to be rougher than other regions of the external component 410. In some embodiments, the texture may be designed to increase the friction of the gripping region 420 such that the user can more easily grip the connector 400.

The component parts of the connector 200, 300, 400 may be formed from polypropylene or other suitable plastics material, for example polyethylene, polycarbonate, acrylonitrile butadiene styrene (ABS), or other thermoplastics or engineering plastics materials. In some embodiments, the external part may comprise over moulded resilient material, for example an over moulded thermoplastic elastomer, in the gripping region 220, to provide improved gripping surfaces, and/or to provide a comfortable grip. The over moulding resilient material may be coloured to denote a particular size of connector. Good bonding can be achieved between thermoplastic elastomers over moulded to plastics such as polypropylene.

The plastics material and/or the resilient material of the external component may include a surface roughness to make the connector easier to grip/grasp and manipulate. For example, a moulding surface of a tool for forming the connector may be formed by bead blasting to roughen the surface of the tool to impart a preferred surface finish to the external component in the gripping region of the external component.

It should be noted that various changes and modifications to the presently preferred embodiments described herein will be apparent to those skilled in the art. Such changes and modifications may be made without departing from the spirit and scope of the apparatus and systems of the disclosure and without diminishing its attendant advantages. For instance, various components may be repositioned as desired. It is therefore intended that such changes and modifications be included within the scope of the apparatus and systems of the disclosure. Moreover, not all of the features, aspects and advantages are necessarily required to practice the present apparatus and systems of the disclosure. Accordingly, the scope of the present apparatus and systems of the disclosure is intended to be defined only by the claims that follow.

Reference to any prior art in this specification is not, and should not be taken as, an acknowledgement or any form of suggestion that that prior art forms part of the common general knowledge in the field of endeavour in any country in the world.

Wherein the foregoing description reference has been made to integers or components having known equivalents thereof, those integers are herein incorporated as if individually set forth.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to".

The apparatus and system of the disclosure may also be said broadly to consist in the parts, elements and features referred to or indicated in the specification of the application, individually or collectively, in any or all combinations of two or more of said parts, elements or features.

The invention claimed is:

1. A connector for a medical tube or a breathing tube for a respiratory assistance system, comprising:
an internal component and an external component, wherein the internal component has a first end and a second end, and the external component has a corresponding first end and a second end,
the first end of the external component comprising an external coupling face, a first internal coupling face, and a second internal coupling face, and
the second end of the internal component comprising an attachment mechanism configured to attach to a tube, and
wherein the internal component is configured to freely rotate bidirectionally relative to the external component when the internal component is coupled with the external component,
wherein the external coupling face is configured to connect to an end of a first medical tube and the first and second internal coupling faces are configured to connect to an end of a second medical tube.

2. A connector as claimed in claim 1, wherein the external component is a unitary or monolithic or single-piece construction.

3. A connector as claimed in claim 1, wherein the external component is a two-piece construction, said two-piece construction comprising a first piece and a second piece provided in a permanent attachment arrangement with each other once attached to each other.

4. A connector as claimed in claim 1, wherein the external component comprises a gripping region.

5. A connector as claimed in claim 4, wherein the external component comprises a first shoulder at an end of the gripping region to which a user may apply an axial pushing force to the connector when fitting the connector to a coupling interface when gripping the gripping region.

6. A connector as claimed in claim 5, wherein the external component comprises a second shoulder at an opposite end of the gripping region to which a user may apply an axial pulling force to the connector when removing the connector from the coupling interface when gripping the gripping region.

7. A connector as claimed in claim 5, wherein a proximal end of the gripping region has a larger diameter than a distal end of the gripping region, the proximal end being proximal relative to the first end of the external component.

8. A connector as claimed in claim 4, wherein the gripping region comprises one or more indents that may receive one or more fingers of a user when the user grips the gripping region.

9. A connector as claimed in claim 8, wherein the one or more indents comprises a convex or a concavely curved surface in a circumferential direction of the external component.

10. A connector as claimed in claim 1, wherein the internal component is coupled to the tube via the attachment mechanism, the attachment mechanism comprising a thread on at least part of the internal component.

11. A connector as claimed in claim 1, wherein the attachment mechanism is located on an attachment region of the internal component, and the attachment region comprises a tapered profile, and wherein the tapered profile comprises a proximal end that has a larger diameter than a distal end.

12. A connector as claimed in claim 1, wherein the external coupling face comprises an external taper.

13. A connector as claimed in claim 1, wherein the external coupling face is an outer surface of an outer wall of the external component.

14. A connector as claimed in claim 13, wherein the first internal coupling face is an outer surface of an inner wall of the external component and the second internal coupling face is an inner surface of the outer wall of the external component.

15. A connector as claimed in claim 1, wherein the internal and external components are configured so that a clearance between the internal and external components allows for relative rotation between the internal and external components.

16. A connector as claimed in claim 15, wherein the internal component is coupled to the external component for relative rotation there between via a ridge on the internal component and a corresponding groove on the external component, or a ridge on the external component and a corresponding groove on the internal component, and wherein the clearance is between the ridge and the groove, wherein the groove and ridge are located adjacent the first end of the internal component.

17. A connector as claimed in claim 1, wherein the external component is a single integrally formed part or piece.

18. A connector as claimed in claim 1 wherein the external component comprises a cuff and an intermediate portion, the cuff being coupled to the intermediate portion to form a unitary structure or single-piece construction.

19. A connector as claimed in claim 1, wherein the first internal coupling face is opposite and facing the second internal coupling face.

20. A connector as claimed in claim 1, wherein the first internal coupling face and the second internal coupling face are configured to form a cavity that is configured to receive the end of the second medical tube.

21. A connector for a medical tube or a breathing tube for a respiratory assistance system, comprising:
- an internal component and an external component, wherein the internal component has a first end and a second end, and the external component has a corresponding first end and second end,
- the first end of the external component comprising a dual coupling system, and
- the second end of the internal component comprising an attachment mechanism configured to attach to a first tube, and
- wherein the internal component is configured to freely rotate bidirectionally relative to the external component when the internal component is coupled with the external component,
- wherein the dual coupling system comprises an external coupling face, a first internal coupling face, and a second internal coupling face,
- wherein the first internal coupling face is opposite and facing the second internal coupling face to form a cavity between the first and second internal coupling faces,
- wherein the cavity is configured to receive an end of a second tube, and
- wherein the external coupling face is configured to connect to an end of a third tube.

22. A connector as claimed in claim 21, wherein the internal component is coupled to the first tube via the attachment mechanism, the attachment mechanism comprising a thread on at least part of the internal component.

* * * * *